United States Patent
Shukair et al.

(10) Patent No.: US 11,723,600 B2
(45) Date of Patent: Aug. 15, 2023

(54) SYSTEM AND METHOD USED TO DETERMINE TISSUE AND/OR ARTIFACT CHARACTERISTICS

(71) Applicant: Briteseed LLC, Chicago, IL (US)

(72) Inventors: Shetha Shukair, Chicago, IL (US); Amal Chaturvedi, Chicago, IL (US); Hariharan Subramanian, Mundelein, IL (US)

(73) Assignee: Briteseed, LLC, Chicago, IL (US)

( * ) Notice: Subject to any disclaimer, the term of this patent is extended or adjusted under 35 U.S.C. 154(b) by 583 days.

(21) Appl. No.: 16/643,744

(22) PCT Filed: Sep. 5, 2018

(86) PCT No.: PCT/US2018/049520
§ 371 (c)(1),
(2) Date: Mar. 2, 2020

(87) PCT Pub. No.: WO2019/050928
PCT Pub. Date: Mar. 14, 2019

(65) Prior Publication Data
US 2020/0268311 A1   Aug. 27, 2020

Related U.S. Application Data

(60) Provisional application No. 62/554,556, filed on Sep. 5, 2017.

(51) Int. Cl.
*A61B 5/00* (2006.01)
*A61B 17/29* (2006.01)
(Continued)

(52) U.S. Cl.
CPC .......... *A61B 5/6847* (2013.01); *A61B 5/0086* (2013.01); *A61B 5/489* (2013.01);
(Continued)

(58) Field of Classification Search
None
See application file for complete search history.

(56) References Cited

U.S. PATENT DOCUMENTS

| 5,129,400 A | 7/1992 | Makino et al. |
| 5,259,761 A | 11/1993 | Schnettler et al. |

(Continued)

FOREIGN PATENT DOCUMENTS

| EP | 2 353 534 | 8/2011 |
| GB | 1 445 678 | 8/1976 |

(Continued)

OTHER PUBLICATIONS

Examination Report with English translation, counterpart Japanese application No. 2020-513325 (dated Aug. 30, 2022) (6 pages).

(Continued)

*Primary Examiner* — Christopher Koharski
*Assistant Examiner* — Michael S Kellogg
(74) *Attorney, Agent, or Firm* — Cook Alex Ltd.

(57) ABSTRACT

A surgical system used to determine if a vessel is within a region proximate to a working end of a surgical instrument includes at least one light emitter configured to emit light of two different wavelengths. The system also includes at least one light sensor disposed opposite the at least one light emitter, the at least one light sensor configured to detect light at the two different wavelengths and to provide a signal having a pulsatile and a non-pulsatile component for each wavelength. The system further includes a controller coupled to the at least one light sensor and configured to determine and indicate if the vessel is a ureter within the region proximate to the working end of the surgical instrument based on a ratio and a symmetry of a dip in the non-pulsatile component.

10 Claims, 6 Drawing Sheets

(51) Int. Cl.
*A61B 90/00* (2016.01)
*A61B 17/00* (2006.01)

(52) U.S. Cl.
CPC ............ *A61B 17/29* (2013.01); *A61B 90/361* (2016.02); *A61B 2017/00057* (2013.01)

(56) References Cited

U.S. PATENT DOCUMENTS

| | | |
|---|---|---|
| 5,423,321 A | 6/1995 | Fontenot |
| 5,762,609 A | 6/1998 | Benaron et al. |
| 5,769,791 A | 6/1998 | Benaron et al. |
| 5,772,597 A | 6/1998 | Goldberger et al. |
| 5,785,658 A | 7/1998 | Benaron et al. |
| 5,807,261 A | 9/1998 | Benaron et al. |
| 5,987,346 A | 11/1999 | Benaron et al. |
| 6,178,340 B1 | 1/2001 | Svetliza |
| 6,374,128 B1 | 4/2002 | Toida et al. |
| 6,569,104 B2 | 5/2003 | Ono et al. |
| 6,594,518 B1 | 7/2003 | Benaron et al. |
| 6,922,577 B2 | 7/2005 | Nakashima et al. |
| 7,006,861 B2 | 2/2006 | Flock et al. |
| 7,112,201 B2 | 9/2006 | Truckai et al. |
| 7,235,072 B2 | 6/2007 | Sartor et al. |
| 7,515,265 B2 | 4/2009 | Alfano et al. |
| 7,740,591 B1 | 6/2010 | Starr et al. |
| 7,749,217 B2 | 7/2010 | Podhajsky |
| 7,904,138 B2 | 3/2011 | Goldman et al. |
| 7,983,738 B2 | 7/2011 | Goldman et al. |
| 8,058,771 B2 | 11/2011 | Giordano et al. |
| 8,073,531 B2 | 12/2011 | Goldman et al. |
| 8,118,206 B2 | 2/2012 | Zand et al. |
| 8,123,745 B2 | 2/2012 | Beeckler et al. |
| 8,150,500 B2 | 4/2012 | Goldman et al. |
| 8,244,333 B2 | 8/2012 | Wood et al. |
| 8,255,040 B2 | 8/2012 | Goldman et al. |
| 8,295,904 B2 | 10/2012 | Goldman et al. |
| 8,380,291 B2 | 2/2013 | Wood et al. |
| 8,391,960 B2 | 3/2013 | Wood et al. |
| 8,417,306 B2 | 4/2013 | Cheng |
| 8,463,364 B2 | 6/2013 | Wood et al. |
| 8,467,857 B2 | 6/2013 | Kim et al. |
| 8,478,386 B2 | 7/2013 | Goldman et al. |
| 8,483,805 B2 | 7/2013 | Takenoshita et al. |
| 8,483,819 B2 | 7/2013 | Choi et al. |
| 8,489,178 B2 | 7/2013 | Wood et al. |
| 8,586,924 B2 | 11/2013 | Demos |
| 8,649,568 B2 | 2/2014 | Sato |
| 8,649,848 B2 | 2/2014 | Crane et al. |
| 8,682,418 B2 | 3/2014 | Tanaka |
| 8,706,200 B2 | 4/2014 | Goldman et al. |
| 8,712,498 B2 | 4/2014 | Goldman et al. |
| 8,750,970 B2 | 6/2014 | Goldman et al. |
| 8,792,967 B2 | 7/2014 | Sato |
| 8,818,493 B2 | 8/2014 | Goldman et al. |
| 8,838,210 B2 | 9/2014 | Wood et al. |
| 9,526,921 B2 | 12/2016 | Kimball et al. |
| 2002/0169381 A1 | 11/2002 | Asada et al. |
| 2003/0036685 A1 | 2/2003 | Goodman |
| 2003/0036751 A1 | 2/2003 | Anderson et al. |
| 2003/0120306 A1 | 6/2003 | Burbank et al. |
| 2004/0111085 A1 | 6/2004 | Singh |
| 2005/0143662 A1 | 6/2005 | Marchitto et al. |
| 2005/0180620 A1 | 8/2005 | Takiguchi |
| 2006/0020212 A1 | 1/2006 | Xu et al. |
| 2006/0052850 A1 | 3/2006 | Darmos et al. |
| 2006/0100523 A1 | 5/2006 | Ogle et al. |
| 2006/0155194 A1 | 7/2006 | Marcotte et al. |
| 2007/0038118 A1 | 2/2007 | DePue et al. |
| 2009/0018414 A1 | 1/2009 | Toofan |
| 2009/0054908 A1 | 2/2009 | Zand et al. |
| 2010/0222786 A1 | 9/2010 | Kassab |
| 2010/0249763 A1 | 9/2010 | Larson et al. |
| 2011/0021925 A1 | 1/2011 | Wood et al. |
| 2011/0245685 A1 | 10/2011 | Murata et al. |
| 2012/0016362 A1 | 1/2012 | Heinrich et al. |
| 2012/0046555 A1 | 2/2012 | Takamatsu et al. |
| 2012/0143182 A1 | 6/2012 | Ullrich et al. |
| 2012/0172842 A1 | 7/2012 | Sela et al. |
| 2012/0296205 A1 | 11/2012 | Chernov et al. |
| 2013/0102905 A1 | 4/2013 | Goldman et al. |
| 2013/0226013 A1 | 8/2013 | McEwen et al. |
| 2013/0267874 A1 | 10/2013 | Marcotte et al. |
| 2014/0086459 A1 | 3/2014 | Pan et al. |
| 2014/0100455 A1 | 4/2014 | Goldman et al. |
| 2014/0155753 A1 | 6/2014 | McGuire, Jr. et al. |
| 2014/0194751 A1 | 7/2014 | Goldman et al. |
| 2014/0236019 A1 | 8/2014 | Rahum |
| 2014/0276088 A1 | 9/2014 | Drucker |
| 2014/0313482 A1 | 10/2014 | Shahidi et al. |
| 2014/0371527 A1 | 12/2014 | Sato |
| 2015/0011896 A1 | 1/2015 | Yelin et al. |
| 2015/0051460 A1 | 2/2015 | Saxena et al. |
| 2015/0066000 A1 | 3/2015 | An et al. |
| 2017/0181701 A1* | 6/2017 | Fehrenbacher .... A61B 18/1445 |
| 2017/0367772 A1 | 12/2017 | Gunn et al. |
| 2018/0042522 A1 | 2/2018 | Subramanian et al. |
| 2018/0098705 A1 | 4/2018 | Chaturvedi et al. |
| 2018/0289315 A1 | 10/2018 | Chaturvedi et al. |
| 2019/0038136 A1 | 2/2019 | Gunn et al. |
| 2019/0046220 A1 | 2/2019 | Chaturvedi et al. |
| 2019/0175158 A1 | 6/2019 | Chaturvedi et al. |
| 2020/0337633 A1 | 10/2020 | Chaturvedi et al. |
| 2020/0345297 A1 | 11/2020 | Chaturvedi et al. |
| 2021/0068856 A1 | 3/2021 | Gunn et al. |

FOREIGN PATENT DOCUMENTS

| | | | |
|---|---|---|---|
| JP | H10-005245 | 1/1998 | |
| JP | 2003-019116 | 1/2003 | |
| JP | 2009-222676 | 10/2009 | |
| JP | 2010-081972 | 4/2010 | |
| JP | 2014-217707 | 11/2014 | |
| JP | 2015-000093 | 1/2015 | |
| WO | WO98/27865 | 7/1998 | |
| WO | WO2001/060427 | 8/2001 | |
| WO | WO2003/039326 | 5/2003 | |
| WO | WO2004/030527 | 4/2004 | |
| WO | WO2005/091978 | 10/2005 | |
| WO | WO2008/082992 | 7/2008 | |
| WO | WO2009/144653 | 12/2009 | |
| WO | WO2011/013132 | 2/2011 | |
| WO | WO2012/158774 | 11/2012 | |
| WO | WO2013/134411 | 9/2013 | |
| WO | WO2014/194317 | 12/2014 | |
| WO | WO2015/148504 | 10/2015 | |
| WO | WO2016/134327 | 8/2016 | |
| WO | WO2016/134330 | 8/2016 | |
| WO | WO2017/062720 | 4/2017 | |
| WO | WO/2017/062720 | * 4/2017 | ........... A61B 18/085 |
| WO | WO2017/139624 | 8/2017 | |
| WO | WO2017/139642 | 8/2017 | |
| WO | WO2018/044722 | 3/2018 | |
| WO | WO2019/126633 | 6/2019 | |
| WO | WO2019/143965 | 7/2019 | |
| WO | WO2020/041203 | 2/2020 | |
| WO | WO2020/142394 | 7/2020 | |

OTHER PUBLICATIONS

Search Report with English translation, counterpart Japanese application No. 2020-513325 (dated Aug. 22, 2022) (26 pages).

Akl et al., Performance Assessment of an Opto-Fluidic Phantom Mimicking Porcine Liver Parenchyma, J. Bio. Optics, vol. 17(7) 077008-1 to 077008-9 (Jul. 2012).

Comtois et al., A Comparative Evaluation of Adaptive Noise Cancellation Algorithms for Minimizing Motion Artifacts in a Forehead-Mounted Wearable Pulse Oximeter, Conf. Proc. IEEE Eng. Med. Biol. Soc., 1528-31 (2007).

Figueiras et al., Self-Mixing Microprobe for Monitoring Microvascular Perfusion in Rat Brain, Med. Bio. Eng'r Computing 51:103-112 (Oct. 12, 2012).

(56) References Cited

OTHER PUBLICATIONS

Hammer et al., A Simple Algorithm for In Vivo Ocular Fundus Oximetry Compensating for Non-Haemoglobin Absorption and Scattering, Phys. Med. Bio. vol. 47, N233-N238 (Aug. 21, 2002).
Ibey et al., Processing of Pulse Oximeter Signals Using Adaptive Filtering and Autocorrelation to Isolate Perfusion and Oxygenation Components, Proc SPIE, vol. 5702, 54-60 (2005).
Li et al., Pulsation-Resolved Deep Tissue Dynamics Measured with Diffusing-Wave Spectroscopy, Optics Express, vol. 14, No. 17, 7841-7851 (Aug. 21, 2006).
Mendelson et al., In-vitro Evaluation of a Dual Oxygen Saturation/Hematocrit Intravascular Fiberoptic Catheter, Biomed Instrum. Technol. 24(3):199-206 (May/Jun. 1990).
Phelps et al., Rapid Ratiometric Determination of Hemoglobin Concentration using UV-VIS Diffuse Reflectance at Isobestic Wavelengths, Optics Express, vol. 18, No. 18, 18779-18792 (Aug. 30, 2010).
Subramanian, Real Time Perfusion and Oxygenation Monitoring in an Implantable Optical Sensor, Thesis Texas A&M Univ. (Dec. 2004).
Subramanian, Real-Time Separation of Perfusion and Oxygenation Signals for an Implantable Sensor Using Adaptive Filtering, IEEE Trans. Bio. Eng'g, vol. 52, No. 12, 2016-2023 (Dec. 2005).
Subramanian, An Autocorrelation-Based Time Domain Analysis Technique for Monitoring Perfusion and Oxygenation in Transplanted Organs, IEEE Trans. Bio. Eng'g, vol. 52, No. 7, 1355-1358 (Jul. 2005).
International Search Report and Written Opinion, counterpart PCT application PCT/US2018/049520, 12 pages (dated Dec. 12, 2018).

\* cited by examiner

SYSTEM AND METHOD USED TO DETERMINE TISSUE AND/OR ARTIFACT CHARACTERISTICS

The present application is a U.S. National Stage of PCT International Patent App. No. PCT/US2018/049520, filed Sep. 5, 2018, which claims benefit of U.S. Provisional App. No. 62/554,556, filed Sep. 5, 2017, both of which are hereby incorporated herein by reference.

BACKGROUND

This patent is directed to a system and method used to determine characteristics of tissue and/or an artifact, such as a vessel, and in particular to a system used to determine characteristics of tissue and/or an artifact, where the system includes at least one light emitter and at least one light sensor.

The identification of artifacts, and in particular vessels, during surgical procedures can provide valuable information for the surgeon or surgical team. For instance, identification of a blood vessel from a vessel that carries a fluid other than blood may permit the non-blood carrying vessel to be avoided, minimizing the chances of injury to the non-blood carrying vessel. Alternatively, identification of the blood vessels and the non-blood carrying vessels may permit the non-blood carrying vessel to be isolated, instead of avoided.

In regard to identification of the vessel to avoid injury, consider the opportunity for iatrogenic ureteral injury during gynecological, urological and other pelvic region surgeries. Such an injury may occur as a consequence of the surgical procedure. Additionally, because the ureters course close to major blood vessels, such as the uterine arteries, ureteral injury can occur as a consequence of attempts to control bleeding. In particular, when inadvertent intraoperative bleeding obstructs the surgeon's field of view, the surgeon's attempts to control the bleeding by cauterizing, clamping or suturing the blood vessels can lead instead to ureteral injury.

Given the proximity of major blood vessels to the ureters and the obstruction of the surgeon's field of view should bleeding occur, injuries can occur even when the surgeon has a sound understanding of normal anatomy. Aberrant ureteral anatomy occurs in up to 8% of the population, however. When combined with the other factors, the surgeon faces a considerable challenge.

A systematic review of gynecological procedures has determined that ureteral injury occurs in 0.03% to 2.0% of abdominal hysterectomies, 0.02% to 0.5% of vaginal hysterectomies and 0.2% to 6.0% of laparoscopic-assisted vaginal hysterectomies. Considering the factors addressed above, perhaps these figures are not surprising. Because of the physiological importance of the renal system and the significant negative consequences of injury to the same, these rates are particularly sobering.

Ureteral injury can lead to ureteral obstruction (for example, if the ureter is ligated) or discontinuity (if the ureter is resected). If an injury to the ureter has occurred and is unrecognized (for example, if the ureter is crushed), it may lead to the formation of fistulas in addition to obstruction. Certainly, ureteral injury can lead to significant patient morbidity and mortality. In any event, ureter injury will increase the likelihood of hospitalization (if the procedure is performed on an outpatient basis), as well as the duration of the hospital stay.

As set forth in more detail below, the present disclosure describes a system including a detector and method of detecting a vessel embodying advantageous alternatives to the existing methods, which may provide for improved identification for avoidance or isolation of a vessel.

SUMMARY

According to an aspect of the present disclosure, a system used to determine if a vessel is within a region proximate to a working end of a surgical instrument includes at least one light emitter disposed at the working end of the surgical instrument, the at least one light emitter configured to emit light of two different wavelengths. The system also includes at least one light sensor disposed at the working end of the surgical instrument opposite the at least one light emitter, the at least one light sensor configured to detect light at the two different wavelengths and to provide a signal having a pulsatile and a non-pulsatile component for each wavelength. The system further includes a controller coupled to the at least one light sensor and configured to determine a ratio of the transmitted light at two different wavelengths, to determine if a dip is present in the non-pulsatile component of the signal from the at least one light sensor for each of the two different wavelengths, to determine a symmetry of the dip if a dip is determined, and to indicate if the vessel is a ureter within the region proximate to the working end of the surgical instrument based on the ratio and the symmetry.

According to another aspect of the present disclosure, a method of determining if a vessel is within a region proximate to a working end of a surgical instrument includes administering a dye, emitting light at two different wavelengths at the working end of the surgical instrument, and sensing light at the two different wavelengths at at least one light sensor at the working end of the surgical instrument. The method further includes determining a ratio of the light transmitted at the least two different wavelengths, determining a dip in a non-pulsatile component of a signal from the at least one light sensor, determining a symmetry of the dip if a dip is determined, and indicating if the vessel is a ureter within the region proximate to the working end of the surgical instrument based on the ratio and the symmetry.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION OF VARIOUS EMBODIMENTS

The embodiments described herein provide systems and methods used to determine characteristics of tissue and/or artifacts in a surgical field.

Figure 1:
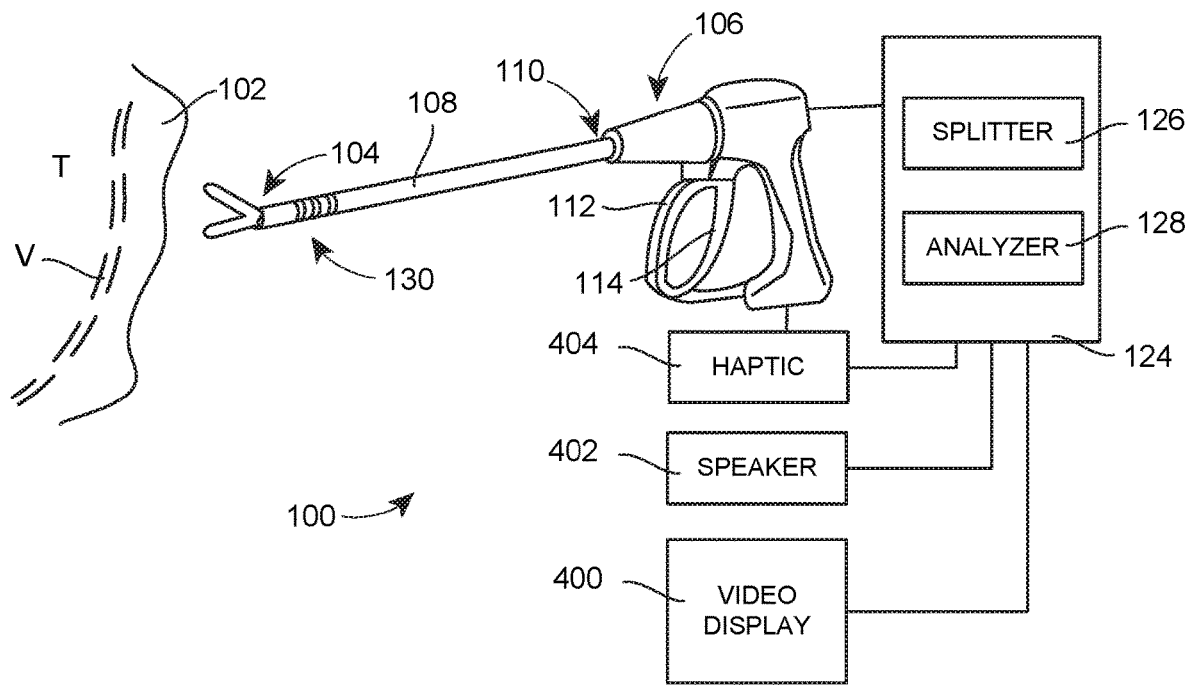
FIG. 1 is a schematic diagram of a surgical system according to an embodiment of the present disclosure.
Figure 2:
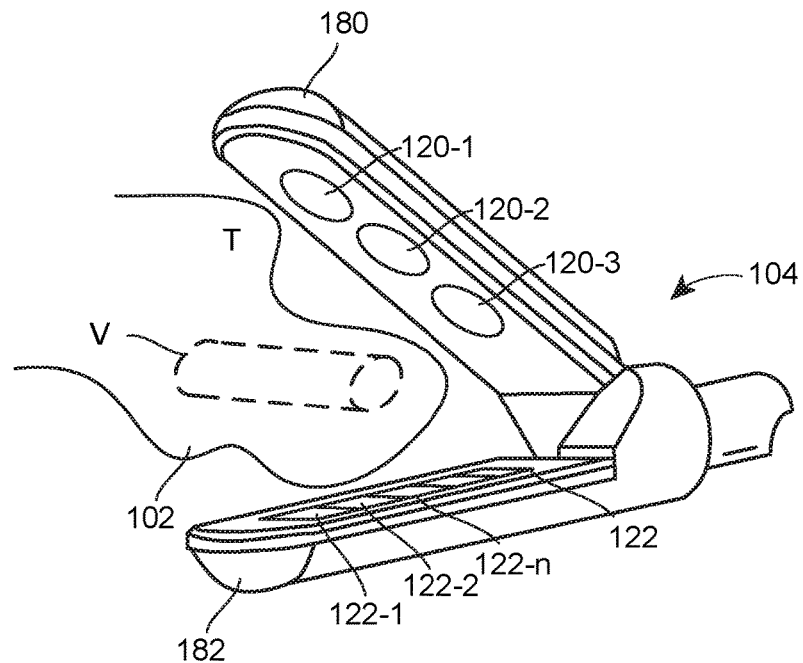
FIG. 2 is an enlarged, fragmentary view of a transmittance-based embodiment of the surgical instrument of FIG. 1 with light emitters and light sensors, and a section of a vessel illustrated as disposed between the light emitters and light sensors.

Turning first to FIGS. 1 and 2, embodiments of a surgical system 100 are illustrated, which system 100 may be used to determine, for example, a characteristic (e.g., presence, diameter, etc.) of a vessel, V, within a region 102 of tissue, T, proximate to a working end 104 of a surgical instrument 106. It will be understood that the vessel V may be connected to other vessels with the region 102 of tissue T, and in addition, the vessel V may extend beyond the region 102 so as to be in fluid communication with other organs (e.g., the kidney, the bladder or the heart) also found in the body of the patient. Furthermore, while the tissue T appears in FIGS. 1 and 2 to surround fully the vessel V (in terms of both circumference and length) to a particular depth, this need not be the case in all instances where the system 100 is used. For example, the tissue T may only partially surround the circumference of and/or only surround a section of the length of the vessel V, or the tissue T may overlie the vessel V in a very thin layer. As further non-limiting examples, the vessel V may be a blood vessel, and the tissue T may be connective tissue and/or adipose tissue.

According to the illustrated embodiments, the working end 104 of the surgical instrument 106 is also a distal end of a shaft 108. Consequently, the working end and the distal end will be referred to as working end 104 or distal end 104. The shaft 108 also has a proximal end 110, and a grip or handle 112 (referred to herein interchangeably as grip 112) is disposed at the proximal end 110 of the shaft 108. The grip 112 is designed in accordance with the nature of the instrument 106; as to the thermal ligation device illustrated in FIG. 1, the grip 112 may be a pistol-type grip including a trigger 114. As an alternative, finger rings arranged in a generally scissors-type grip may be used.

While the working or distal end 104 and the proximal end 110 with grip 112 are illustrated as disposed at opposite-most ends of the shaft 108, it will be recognized that certain surgical instruments have working ends (where a tool tip is attached, for example) disposed on the opposite-most ends of the shaft and a gripping region disposed intermediate to the opposite working ends. In accordance with the terms "distal" and "proximal" as used herein, the working ends of such an instrument are referred to herein as the distal ends and the gripping region as the proximal end. Relative to the illustrated embodiments, however, the distal and proximal ends are located at opposite-most (or simply opposite) ends of the shaft 108.

As mentioned above, according to the embodiments illustrated, the surgical system 100 includes a sensor with at least one light emitter 120 (or simply the light emitter 120) and at least one light sensor or detector 122 (or simply the light sensor 122). See FIG. 2. As illustrated, the light emitter 120 is disposed at the working end 104 of the surgical instrument 106, and the light sensor 122 is also disposed at the working end 104 of the surgical instrument 106. The system 100 operates according to a transmittance-based approach, such that the light sensor(s) 122 is/are disposed opposite and facing the light emitter(s) 120, for example on opposite jaws of a surgical instrument 106 as illustrated in FIG. 2.

The light emitter 120 is configured to emit light of at least two different wavelengths, and the light sensor 122 is configured to detect light at the at least two different wavelengths. As one example, the light emitter 120 may emit and the light sensor 122 may detect light in the visible range and light in the near-infrared or infrared range. Specifically, the light emitter 120 may emit and the light sensor 122 may detect light at 660 nm and at 810 nm.

According to the illustrated embodiments, the individual light sensor 122 is configured to generate a signal comprising a first pulsatile component and a second non-pulsatile component. It will be recognized that the first pulsatile component may be an alternating current (AC) component of the signal, while the second non-pulsatile component may be a direct current (DC) component. Where the light sensor 122 is in the form of an array, the pulsatile and non-pulsatile information may be generated for each element of the array, or at least for each element of the array that defines the at least one row of the array.

According to such embodiments, the controller 124 is coupled to the light sensor 122, and the splitter 126 is used to separate the first pulsatile component from the second non-pulsatile component for each element of the light sensor array 122. The controller 124 may also include an analyzer 128 to determine the presence of and/or characteristic(s) of the vessel V within the region 102 proximate to the working end 104 of the surgical instrument 106 based (at least in part) on the pulsatile component.

Figure 4:
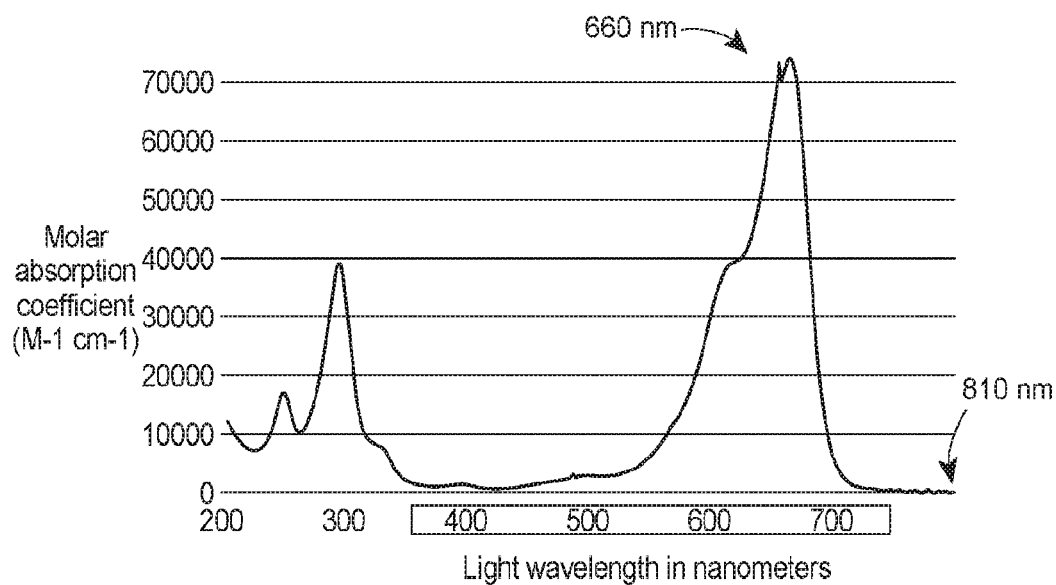
FIG. 4 is a chart illustrating the light absorption spectrum of methylene blue.
Figure 5:
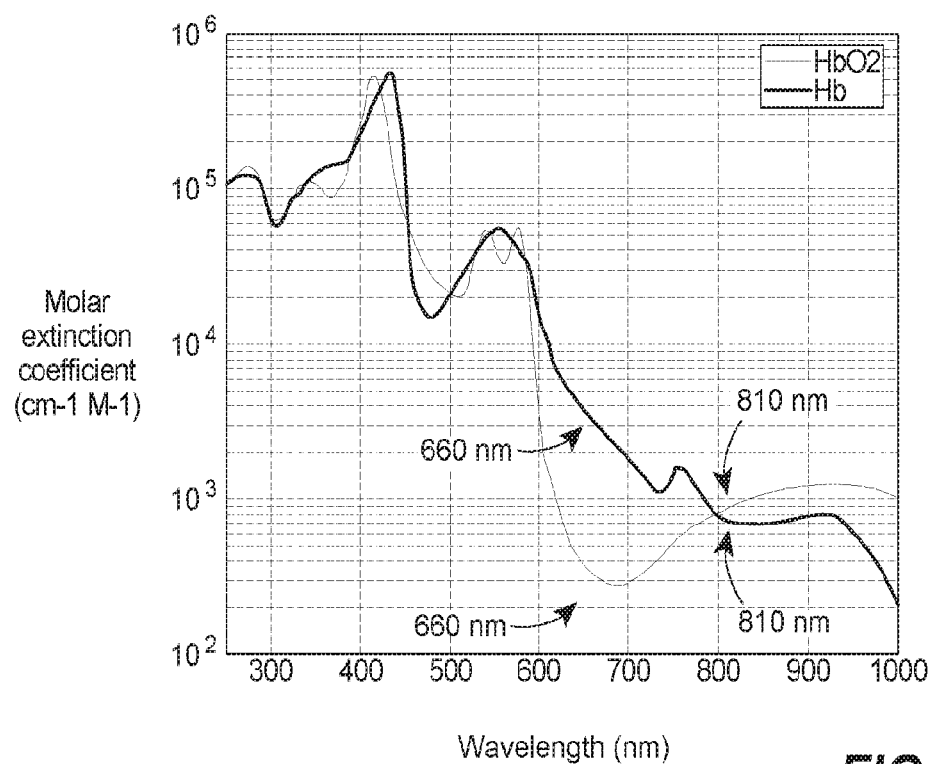
FIG. 5 is a chart illustrating the light absorption spectrum of blood.

The embodiments of the present disclosure according to FIGS. 1-3 may be discussed in general terms as follows. Light of different wavelengths is absorbed by blood (within blood vessels or potentially bleeding from the blood vessels into the surgeon's field of view), static tissue (e.g., fat, connective tissue, etc.) or the ureter to different extents. By selecting a pair of wavelengths where the absorption of light is similar for blood but significantly different for fluid in the ureter (e.g., a dye, or even urea), the system 100 and method 150 may differentiate between blood or a blood vessel and a ureter. For example, if a contrast agent such as methylene blue is administered to the patient (which collects quickly in the ureter), the ratio of light transmitted at wavelengths of 660 nm and at 810 nm will be small for the ureter (e.g., less than 1) and larger for blood or a blood vessel (e.g., greater than 1.5). Compare the absorption coefficients for methylene blue and blood at these wavelengths in FIGS. 4 and 5. As a consequence, a relatively robust differentiation may be made between an artifact 120 in the form of a ureter and blood in the surgeon's field of view. In this regard, U.S. Publ. No. 2017/0181701 is incorporated by reference herein in its entirety.

The discrimination between blood vessel, ureter and tissue may be improved by recognizing that the non-pulsatile (or DC) component of the signal from the light sensor(s) 122 is not the same for a blood vessel, a ureter and other tissue. The DC signal will experience a dip in signal if a vessel, such as a blood vessel or ureter, is present between the jaws of the surgical device 106, while the dip will not appear if tissue without a blood vessel or ureter is present. Furthermore, the DC signal for a ureter has dips that are more asymmetrical than those of blood vessels, and the signal or a ureter may even have multiple dips. Using this information, a method for making an even more robust differentiation may be proposed.

In particular, the controller 124 may be configured to determine a ratio of the light transmitted at at the least two different wavelengths a well as a symmetry metric, and to indicate if a vessel V within a region 102 proximate to the working end 104 of the surgical instrument 106 is, for example, a ureter based on the ratio and the symmetry metric. Instead of being a ureter, the artifact (or structural artifact) may be a blood vessel or a tissue. Based on this indication, which may be provided by a visual indicator 130 (see FIG. 1), for example, the surgeon may take the appropriate action.

Figure 3:
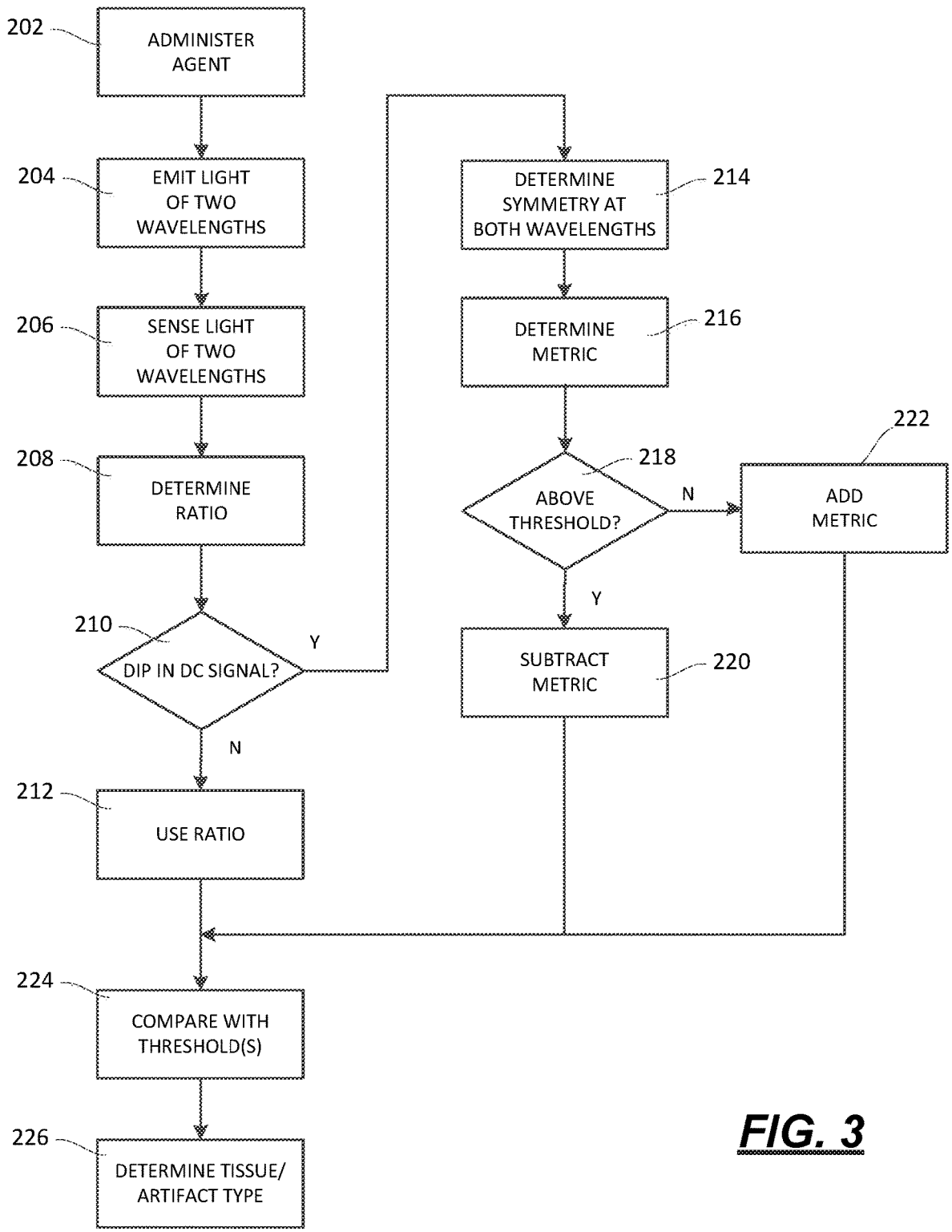
FIG. 3 is a flow chart of a method of detecting a vessel (e.g., a ureter) according to an embodiment, which method may be carried out using the system of FIG. 1.

As reflected in the flowchart of FIG. 3, a method 200 of determining if a ureter is within a region 102 proximate to a working end 104 of a surgical instrument 106 is illustrated, and may be carried out using the surgical system 100 described in regard to FIGS. 1 and 2. The method 200 may begin at block 202, wherein an agent is administered to the patient undergoing the procedure. For example, indigo carmine has a characteristic light absorption at 600 nm, while methylene blue has a characteristic light absorption at 660 nm (see FIG. 4). These dyes have the benefit that they are typically used for the visual identification of ureter and bladder leakage during surgery, and thus do not represent an additional burden in terms of additional procedural steps or expense.

The method continues at block 204, wherein light of at least two different wavelengths is emitted at the working end 104 of the surgical instrument 106, for example using the light emitter 120. The method 200 continues at block 206, wherein light of at least two different wavelengths is sensed at the working end 104 of the surgical instrument 106, for example using the light sensor 122. While the actions of blocks 204 and 206 are illustrated appear sequential, the actions may instead occur simultaneously instead of sequentially. That is, the light may be emitted and detected successively using electronic multiplexing or simultaneously via use of optical filters.

The method 200 further includes determining a ratio of the light transmitted at the at least two different wavelengths at block 208. While a determination may be made at this point to determine if there is tissue, ureter or blood vessel between the jaws of the surgical instrument 106, the method 200 continues on with additional steps that may provide greater discrimination between those signals representative of tissue, ureter or blood vessel, providing for a more robust overall determination. Thus, the ratio determined at block 208 may be combined with information regarding the non-pulsatile, or DC, signal along the light sensor 122 (in the form of an array of individual light sensors) to make the determination regarding the identification of the tissue, ureter, or blood vessel between the jaws of the surgical instrument 106.

According to the illustrated embodiment, the controller 124 analyzes the DC signal from the light sensor 122 to determine if there is a decrease in the signal between one end of the light sensor 122 and the other (e.g., between one end of a linear array of individual light sensing elements and the other) at block 210. This determination is performed at both of the two wavelengths. If there are no dips, then the method 200 proceeds to block 210, and the ratio determined at block 208 is used in the remainder of the method 200. If there have been one or more decreases ("dips") in the DC signal for at least one of the wavelengths, then the method proceeds to block 214.

At block 214, the controller determines the degree of symmetry apparent in the dips in the DC signal. This determination occurs at both wavelengths. The symmetry determinations are then combined into a single symmetry metric at block 216. The symmetry metric is first compared against a threshold value at block 218, and depending on whether the metric is above or below a threshold, the metric is either subtracted from the ratio determined at block 208 (block 220) or added to the ratio determined at block 208 (block 222).

The ratio, modified as may be determined at block 220 or 222, is then compared to one or more thresholds at block 224 and the tissue or artifact type determined at block 226. For example, a ratio below a first threshold may be representative of a ureter, a ratio above a second threshold may be representative of a blood vessel, and a ratio between the first and second thresholds may be tissue.

According to one embodiment, if it is determined at block 226 that the artifact is not a ureter, the method 150 may return to block 202, to repeat the actions of blocks 204-226. According to another embodiment, if the artifact is a ureter and an indicator 130 is activated for a time period, which may be followed by the method returning to block 202. For example, according to an embodiment of the method 200 where the indicator is a lockout device that disables the medical instrument 106 for a time period, the method 200 may return to block 202 once the lockout device has been deactivated. As another example, according to an embodiment wherein the indicator is a speaker that generates an audible alarm, the method 200 may activate the indicator/speaker for a period of time (e.g., 1-2 seconds), then repeat the actions of blocks 202-226 and activate the indicator again if the determination is made at block 226 that the ureter is in the region 102. If the blocks 202-226 are repeated and the ureter is not in the region 102, then the method 200 would not re-activate the indicator according to such an embodiment.

Having discussed the structure and operation of the system 100 in general term, further details regarding the system and method are now provided.

Returning to FIGS. 1 and 2, the light emitter 120 may include one or more elements, as referenced above. According to an embodiment schematically illustrated in FIG. 2, the light sensor 122 may include a plurality of light emitters, such as a first light emitter 120-1, a second light emitter 120-2, and a third light emitter 120-3. All of the light emitters may be configured to emit light at a particular wavelength (e.g., 660 nm), or certain emitters may emit light at different wavelengths than other emitters. Each light emitter may be a light emitting diode, for example.

As to those embodiments wherein the light emitter 120 is in the form of an array including one or more light emitting diodes, as is illustrated in FIG. 2, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 122 also may include one or more elements. Again, according to the embodiment illustrated in FIG. 2, the light sensor 122 may include a first light sensor 122-1, a second light sensor 122-2, an n-th light sensor 122-n, and so on. As was the case with the light emitters 120-1, 120-2, 120-3, the light sensors 122-1, 122-2, 122-3, 122-n may be arranged in an array, and the discussion about the arrays above applied with equal force here.

In fact, where the array of light sensors 122 includes a row of light sensors (such as in FIG. 2), the array 122 may be referred to in the alternative as a linear array. The individual light sensors of the array 122 may be disposed adjacent each other, or the light sensors may be spaced from each other. It may even be possible for the individual light sensors that define a row of light sensors to be separated from each other by light sensors that define a different row or column of the array. According to a particular embodiment, however, the array may comprise a charge coupled device (CCD), and in particular linear CCD imaging device comprising a plurality of pixels. As a further alternative, a CMOS sensor array may be used.

The system 100 may include hardware and software in addition to the emitter 120, sensor 122, and controller 124. For example, where more than one emitter 120 is used, a drive controller may be provided to control the switching of the individual emitter elements. In a similar fashion, a multiplexer may be provided where more than one sensor 122 is included, which multiplexer may be coupled to the sensors 122 and to an amplifier. Further, the controller 124 may include filters and analog-to-digital conversion as may be required.

According to certain embodiments, the splitter 126 and the analyzer 128 may be defined by one or more electrical circuit components. According to other embodiments, one or more processors (or simply, the processor) may be programmed to perform the actions of the splitter 126 and the analyzer 128. According to still further embodiments, the splitter 126 and the analyzer 128 may be defined in part by electrical circuit components and in part by a processor programmed to perform the actions of the splitter 126 and the analyzer 128.

For example, the splitter 126 may include or be defined by the processor programmed to separate the first pulsatile component from the second non-pulsatile component. Further, the analyzer 128 may include or be defined by the processor programmed to determine the presence of (or to quantify the size of, for example) the vessel V within the region 102 proximate to the working end 104 of the surgical instrument 106 based on the first pulsatile component. The instructions by which the processor is programmed may be stored on a memory associated with the processor, which memory may include one or more tangible non-transitory computer readable memories, having computer executable instructions stored thereon, which when executed by the processor, may cause the one or more processors to carry out one or more actions.

As regards the agents that may be used, the agents mentioned above, indigo carmine and methylene blue, may be injected into the blood stream, and then quickly accumulate in the kidneys, where the agents and/or their derivatives are excreted by the renal system in urine through the ureters, bladder and urethra (in this regard, it will be recognized that certain agents may be metabolized in the body; for example, methylene blue is excreted as leukomethylene blue by the kidneys). On the other hand, if the dye is administered continuously intravenously throughout a surgery, the ureter may be identified throughout the surgery, and not simply within a particular time window after a bolus injection has been administered, which is an advantage particular to this system 100 and method.

It also will be noted that the surgical system 100 according such an embodiment provides the advantage of permitting differentiation between not only blood in blood vessels, but blood in the surgical field. As mentioned above, there is often a loss of direct visualization of the ureters because of blood obstructing the surgeon's field of view. In this case, the use of the ratio(s), between light in the visible spectrum and light in the infrared or near-infrared spectrum, in combination with the high absorptivity of near-infrared light by dyes (such as methylene blue) permits a robust differentiation to be made between the ureter and the stagnant blood in the surgeon's field of view. Consequently, it is believed that stagnant blood will not represent a significant obstacle for the surgeon using the system 100 and method 150 according to the present disclosure.

It is further noted that though dye may be used, if the dye becomes present in the surgical field in the form of stagnant blood for example, it is believed that the surgical instrument according to the above embodiments may still differentiate the dye present in the blood from the dye in the ureter. First, the concentration of dye in the blood vessel, and thus in the stagnant blood, is more dilute than that found in the kidneys and resultantly in the ureters. As a consequence, any variance in the light measured and the resultant signal passed to the controller may be filtered as noise. Second, dyes such as methylene blue have a modified absorption profile at different levels of acidity or basicity, which levels are normally expressed in terms of pH. For example, blood has a pH of approximately 7.3 (relatively neutral), while urine has a pH of 4.6 (acidic). This permits the wavelengths to be used in determining the ratio to be selected in such a manner as to increase the likelihood that a determination that an artifact is a ureter is an accurate determination even if there is dye present in blood as well.

As to issue of identification of dips in the non-pulsatile component of the signal from the light sensors 122, PCT Appl. Nos. PCT/US16/18805, filed Feb. 19, 2016, and PCT/US16/55910, filed Oct. 7, 2016, are each incorporated herein by reference in their entirety. In particular, as it relates to the method 200, it will be recognized from these applications and U.S. Publ. No. 2017/0181701 that tissue without a vessel, such as a blood vessel or a ureter, does not exhibit a dip, or decrease, in signal level. When this occurs, the ratio does not need to be altered as the signal is representative of tissue, and not a ureter or blood vessel (see blocks 210, 212 of method 200 in FIG. 3).

Figure 6:
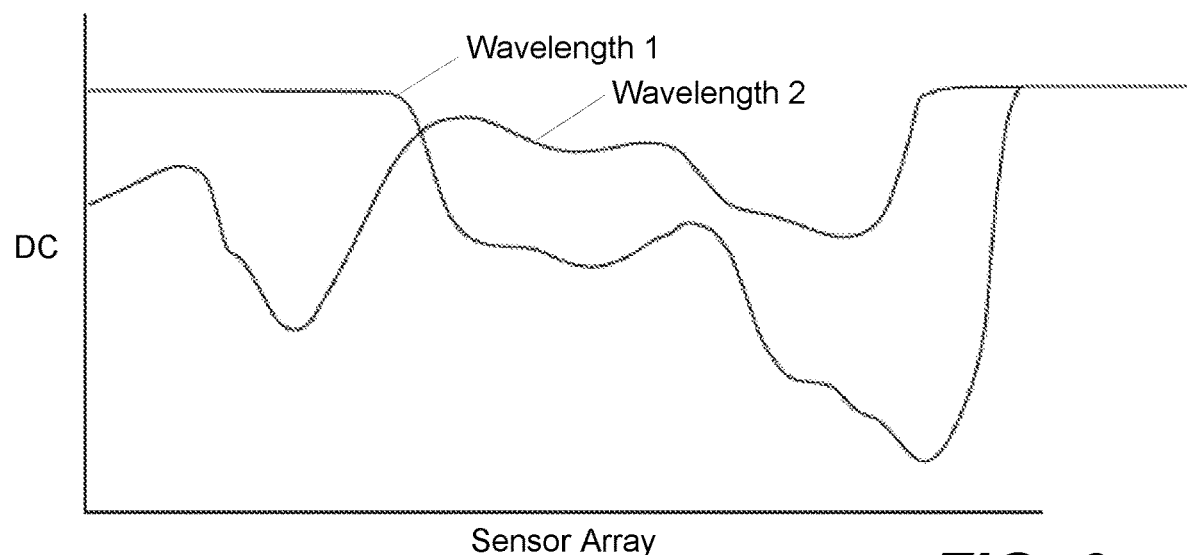
FIG. 6 is a signal profile of a non-pulsatile component of a signal from a light sensor in the presence of a ureter at two wavelengths.

On the other hand, a vessel such as a blood vessel or a ureter will exhibit a dip in the non-pulsatile (or DC) signal level across the light sensor 122 in the presence of the vessel. The dip that appears in the presence of a ureter is considerably different than the dip that appears in the presence of a blood vessel, however. The dip that appears in the signal in the presence of a ureter, both for the visible and near-infrared wavelengths, along the light sensor 122 is more asymmetrical for a ureter than a blood vessel. Compare FIGS. 6 (ureter) and 7 (blood vessel).

Figure 7:
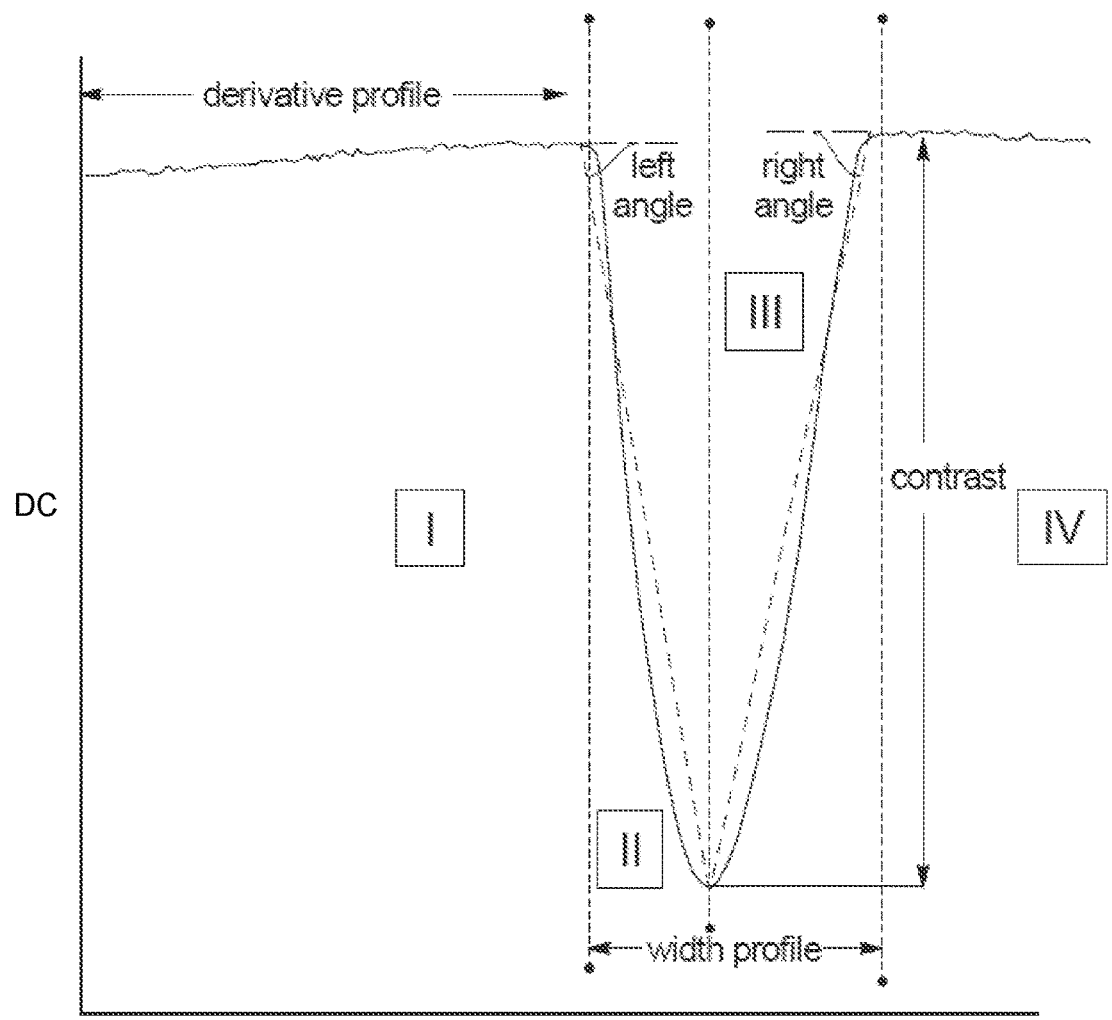
FIG. 7 is a signal profile of a non-pulsatile component of a signal from a light sensor in the presence of a blood vessel at one wavelength.

The method 200 considers and quantifies the symmetry at blocks 214, 216 so that the symmetry can be used computationally with the ratio determined at block 208 to determine the identity of the vessel, if one exists. According to one embodiment, the symmetry is quantified by using the distances from a light sensor at either edge of the dip to a light sensor associated with the minimum of the dip in the signal along the light sensors 122. For the profile in FIG. 6, it will be recognized that the distances from the light sensor at the right edge of the dip to the light sensor associated with the minimum and from the light sensor at the left edge of the dip to the light sensor associated with the minimum are very different. On the other hand, for the profile in FIG. 7, it will be recognized that the distances from the light sensor at either the right edge or the left edge to the light sensor associated with the minimum are relatively similar.

According to this embodiment, after determining the light sensors at the edges of the dip and the light sensor associated with the minimum at each of the wavelengths, the distances are determined between the edges and the minimum, and the differences between those distances are determined. The larger the asymmetry in the signal, the larger the difference, such that the ureter should have a larger difference in the distances from right and left edge to the minimum than a blood vessel. These differences are then used as the determination of the symmetry at block 214.

At block 216, the metric is defined by adding the differences determined at each of the wavelengths. Again, as a greater asymmetry is expected in the signal for the ureter, it is expected that the metric will be larger for the ureter than the blood vessel. This metric is then compared at block 218 to a threshold. Considering the expected differences in the metric based on the relative level of symmetry and asymmetry, the comparison should show a definite difference between the metrics for ureter and blood vessel.

Finally, at blocks 220, 222, a value is either added or subtracted to the ratio based on the comparison of the metric with the threshold at block 218. According to the illustrated embodiment, the metric itself is used to modify the ratio, although according to other embodiments, a predefined value could be used to add and/or subtract from the ratio.

Further, while the method 200 provides one mechanism for quantifying symmetry for use in differentiating between tissue, ureter and blood vessel, this is not the only mechanism for doing so. For example, the ureter DC signal often exhibits multiple dips, and this information combined with the nature of the surgery and the ratio may be used to differentiate between tissue, ureter and blood vessel.

While the discussion above has been primarily for distinguishing a ureter from a blood vessel or other tissue, it may be possible to adapt this technology to distinguish or differentiate other structures as well. For example, one might be able to adapt this technology to distinguish bile ducts or lymphatic vessels.

For example, in regard to bile duct identification, indocyanine green (ICG) fluorophore (e.g., indocyanine green/lipophilic substance VM674, available from VisEn Medical, Bedford, Mass.) may be used in a fashion similar to indigo carmine and methylene blue were used relative to ureters, above, with reference to the absorptive properties of the fluorophore. The indocyanine green fluorophore may be conjugated with a lipophile to promote hepatobiliary excretion or injected directly into the gallbladder.

Figure 8:
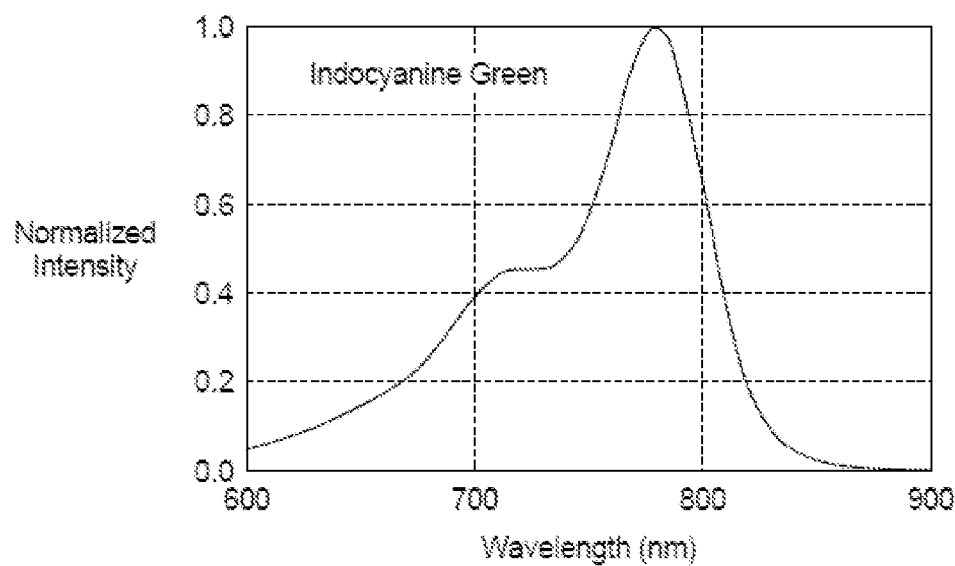
FIG. 8 is a chart illustrating the light absorption and emission spectra of indocyanine green.

FIG. 8 is a chart of the absorption and emission spectra of indocyanine green, with the absorption spectrum on the left and the emission spectrum on the right. It will be recognized that there is a significant narrow peak in the absorption spectrum at a wavelength of 780 nm, relative to the absorption at 660 nm, for example. It is believed that the detected transmitted light at wavelengths of 780 nm and 660 nm will result in a ratio of less than 1, while the ratio of transmitted light for blood or a blood vessel should be considerably more (e.g., more than 1 to 1.5).

It may be possible to use other fluorophores or chromophores, depending on their absorption profiles. For example, methylene blue may be used. It will be recognized that methylene blue has been used previously for the coloration of the biliary tree. The methylene blue may be injected directly into the gallbladder, similar to the introduction method described above relative to indocyanine green.

Of course, where a particular fluorophore or chromophore has become established for use in procedures related to the gallbladder, this may provide an incentive to use the fluorophore or chromophore with the systems and methods described herein. That is, use of such a fluorophore or chromophore would simplify the procedure generally by eliminating the need to inject and detect multiple agents. Moreover, such a fluorophore may be used with intraoperative fluorescent imaging systems (such as the SPY Imaging System available from Novadaq of Mississauga, Ontario, Canada) so that the imaging system may provide a perspective of the entire cutting field, while the system according an embodiment of the present disclosure may provide information regarding the artifacts (in particular vessels) proximate to the working end of the surgical instrument.

As another example, Patent Blue V may be used in regard to lymphatic vessel identification. Other alternatives include Evans blue and methylene blue, as well as indocyanine green. Patent Blue V and these other alternatives have the advantage, mentioned above, of being used in regard to lymphography at the present time, providing the incentives mentioned above for established fluorophores or chromophores.

Figure 9:
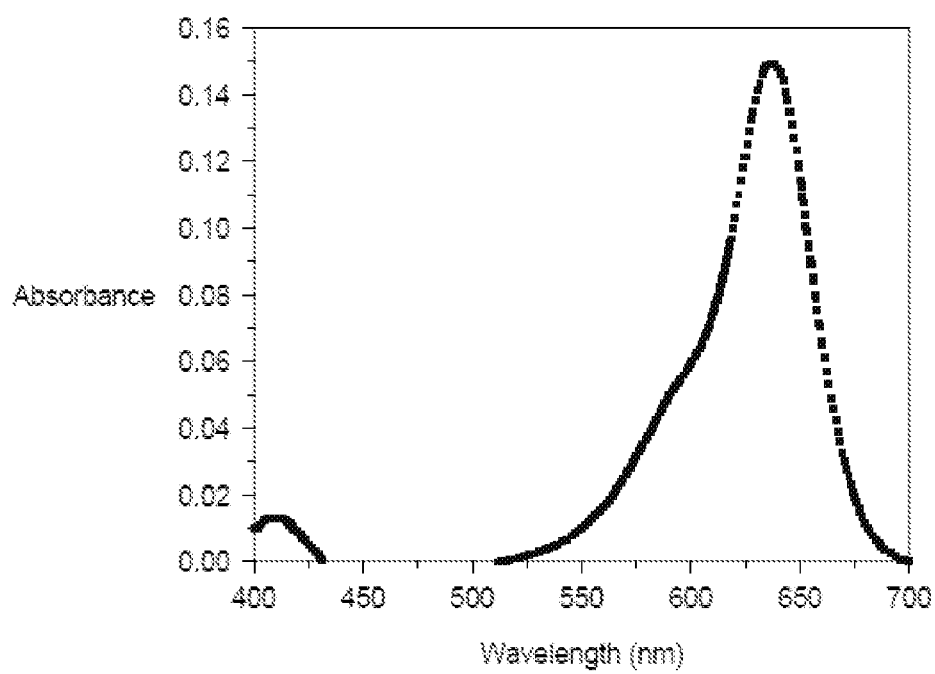
FIG. 9 is a chart illustrating the light absorption spectrum of Patent Blue V.

FIG. 9 is a chart of the absorption spectrum of Patent Blue V. It will be recognized that there is a significant peak in the absorption spectrum at a wavelength of 640 nm, relative to the absorption at 700 nm, for example. It is believed that the detected transmitted light at wavelengths of 640 nm and 700 nm will result in a ratio less than 1, while the ratio of transmitted light for blood or a blood vessel should be considerably more (e.g., more than 1 or 1.5). As will be recognized from the discussion above, if indocyanine green is used instead, the ratio might be determined at 780 nm and 660 nm instead.

Figure 10:
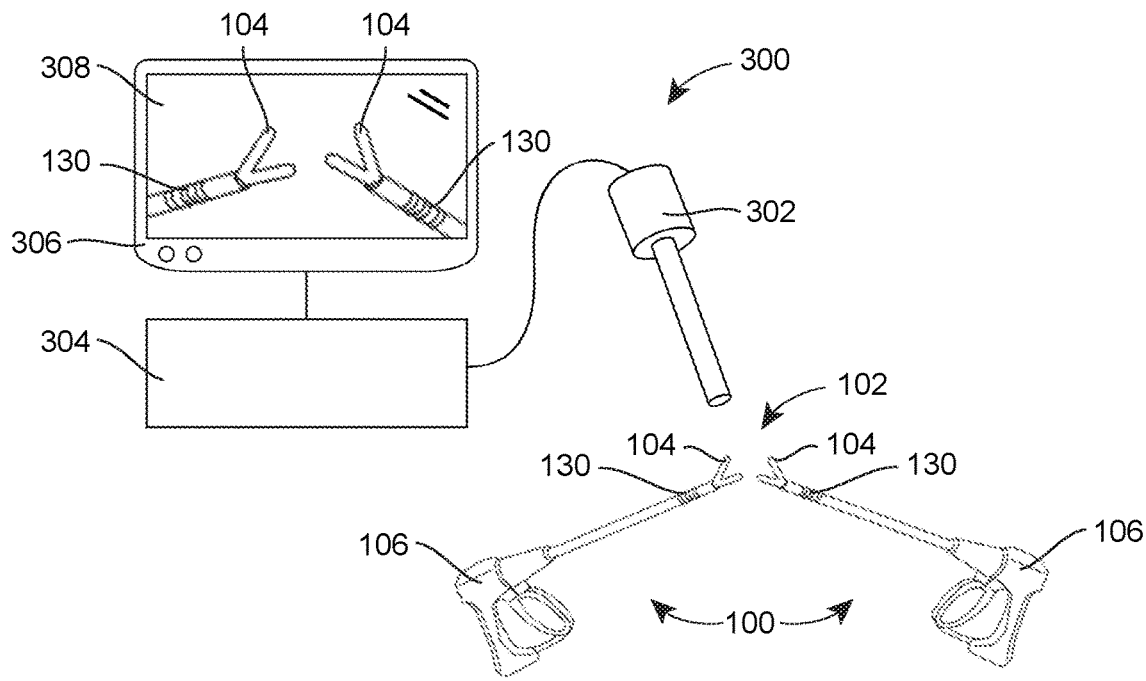
FIG. 10 is a schematic diagram of a surgical system according to an embodiment of the present disclosure, in combination with an embodiment of a video system, illustrating the surgical system in use with the video system.
Figure 11:
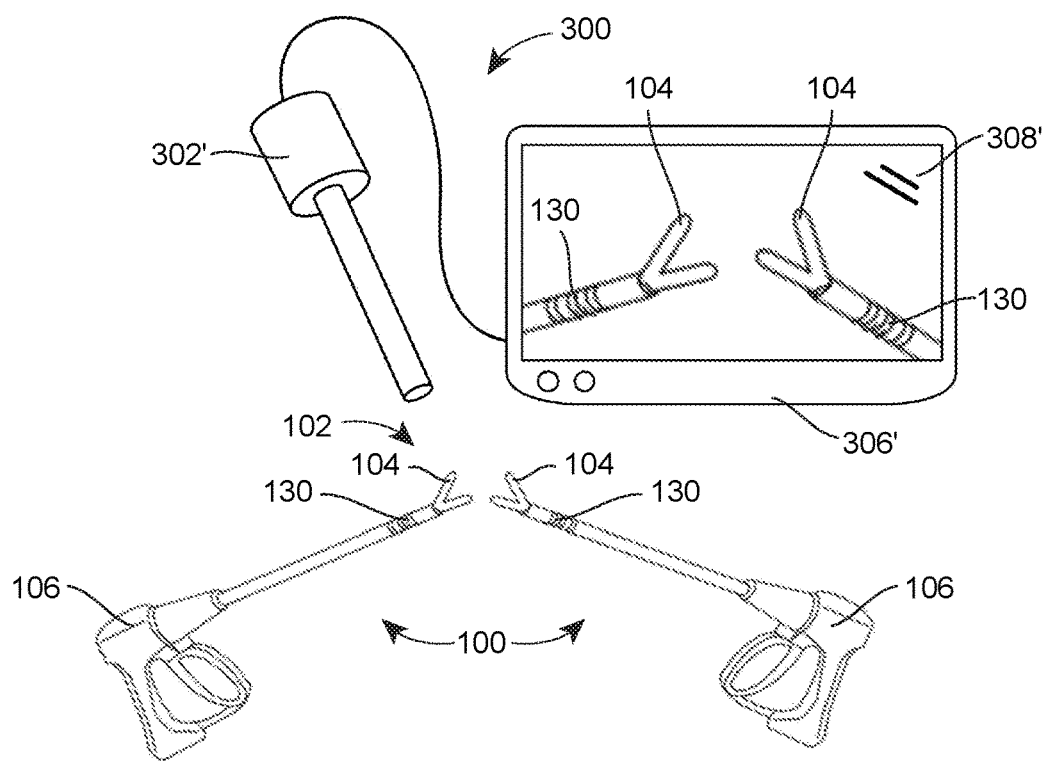
FIG. 11 is a schematic diagram of a surgical system according to an embodiment of the present disclosure, in combination with another embodiment of a video system, illustrating the surgical system in use with the video system.

FIGS. 10 and 11 illustrate an embodiment of the surgical system 100 in combination with embodiments of a video system 300, such as may be used conventionally during minimally invasive surgery or laparoscopic surgery, for example. The video system 300 includes a video camera or other image capture device 302, a video or other associated processor 304, and a display 306 having a viewing screen 308.

As illustrated, the video camera 302 is directed at the region 102 proximate the working ends 104 of two surgical instruments 106. As illustrated, both of the surgical instruments 106 are part of an embodiment of a surgical system 100, such as illustrated in FIG. 2 and discussed above. In this case, the instruments 106 each include a visual indicator 130. It will be recognized, however, that according to other embodiments only one of the instruments 106 may include a visual indicator 130. The other elements of the surgical system 100 are omitted for ease of illustration, although it will be noted that elements of the system 100, such as the splitter 126 and the analyzer 128, may be housed in the same physical housing as the video processor 304.

The signal from the video camera 302 is passed to the display 306 via the video processor 304, so that the surgeon or other member of the surgical team may view the region 102 as well as the working ends 104 of the surgical instruments 106, which are typically inside the patient. Because of the proximity of the visual indicators 130 to the working ends 104, and thus the region 102, the visual indicators 130 are also visible on the display screen 108. As mentioned previously, this advantageously permits the surgeon to receive visual cues or alarms via the visual indicators 130 via the same display 306 and on the same display screen 308 as the region 102 and the working ends 104. This, in turn, limits the need of the surgeon to look elsewhere for the information conveyed via the visual indicators 130.

FIG. 11 illustrates another embodiment of a video system 300 that can be used in conjunction with an embodiment of the surgical system 100. According to this embodiment, the video processor 304 is not disposed in a housing separate from the video camera 302', but is disposed in the same housing as the video camera 302'. According to a further embodiment, the video processor 304 may be disposed instead in the same housing as the remainder of the display 306' as the display screen 308'. Otherwise, the discussion above relative to the embodiment of the video system 300 illustrated in FIG. 10 applies equally to the embodiment of the video system 300 illustrated in FIG. 11.

While the user interface 130 advantageously permits the surgeon or surgical team to view an output from the controller 124, it is possible to include other output devices with the user interface 130, as illustrated in FIGS. 1 and 2. For example, an alert may be displayed on a video monitor 400 being used for the surgery (e.g., the display 306, 306' in FIGS. 10 and 11), or may cause an image on the monitor to change color or to flash, change size or otherwise change appearance. The auxiliary output may also be in the form of or include a speaker 402 that provides an auditory alarm. The auxiliary output also may be in the form of or may incorporate a safety lockout associated with the surgical instrument 106 that interrupts use of the instrument 106. For example, the lockout could prevent ligation or cauterization where the surgical instrument 106 is a thermal ligature device. As a still further example, the auxiliary output also may be in the form of a haptic feedback system, such as a vibrator 404, which may be attached to or formed integral with a handle or handpiece of the surgical instrument 106 to provide a tactile indication or alarm. In addition to the light emitting elements disposed at the working end 104 of the surgical instrument 108, one or more light emitting elements may be disposed at the proximal end 110 of the shaft 108, such as disposed on or attached to the grip or handle 112, to provide a visual indication or alarm. Various combinations of these particular forms of the auxiliary output may also be used.

As mentioned above, the surgical system 100 may also include the surgical instrument 106 with the working end 104, to which the user interface 130 and the sensor (and in preferred embodiments, the light emitter 120 and the light sensor 122) are attached (in the alternative, removably/reversibly or permanently/irreversibly). The user interface 130 and sensor may instead be formed integrally (i.e., as one piece) with the surgical instrument 106. As also stated, it is possible that the user interface 130 and sensor be attached to a separate instrument or tool that is used in conjunction with a surgical instrument or tool 106.

As noted above, the surgical instrument 106 may be a thermal ligature device in one embodiment. In another embodiment, the surgical instrument 106 may simply be a grasper or grasping forceps having opposing jaws. According to still further embodiments, the surgical instrument may be other surgical instruments such as irrigators, surgical staplers, clip appliers, and robotic surgical systems, for example. According to still other embodiments, the surgical instrument may have no other function that to carry the user interface and sensor and to place them within a surgical field. The illustration of a single embodiment is not intended to preclude the use of the system 100 with other surgical instruments or tools 106.

In conclusion, although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

What is claimed is:

1. A system used to determine if a ureter is within a region proximate to a working end of a surgical instrument, the system comprising:
    at least one light emitter disposed at the working end of the surgical instrument, the at least one light emitter configured to emit light of two different wavelengths,
    at least one light sensor array disposed at the working end of the surgical instrument opposite the at least one light emitter, the at least one light sensor array configured to detect light at the two different wavelengths, the at least one light sensor array comprising an array of individual light sensors each configured to provide a signal having an alternating current (AC) component and a direct current (DC) component for each wavelength,
    a controller coupled to the at least one light sensor array and configured to determine a ratio of the transmitted light at two different wavelengths, to determine if a dip or decrease in the DC component of the signal between a first end and a second end of the at least one light sensor array is present in the non-pulsatile component of the signal from the individual light sensors of the at least one light sensor array for each of the two different wavelengths, to determine a symmetry of the dip about an axis of symmetry if a dip is determined, and to indicate if the ureter is within the region proximate to the working end of the surgical instrument based on the ratio and the symmetry.

2. The system according to claim 1, wherein the controller is further configured to determine, for each wavelength, a first distance from a light sensor of the at least one light sensor array detecting a first edge of the dip where the dip begins to a light sensor of the at least one light sensor array detecting a minimum of the dip where the DC component is at its lowest value and a second distance from a light sensor of the at least one light sensor array detecting a second edge of the dip where the dip ends to the light sensor detecting the minimum, and to subtract the first distance from the second distance to define a difference.

3. The system according to claim 1, wherein the at least one light sensor array comprises a first light sensor configured to detect light in the visible range and a second light sensor configured to detect light in the near-infrared range.

4. The system according to claim 3, wherein the first light sensor is configured to detect light at 660 nm and the second light sensor is configured to detect light at 810 nm.

5. The system according to claim 1, wherein the controller comprises a processor and non-transitory computer-readable medium, and the processor is programmed to determine a ratio of the transmitted light at the two different wavelengths, to determine a dip in the non-pulsatile component of the signal from the at least one light sensor array, to determine a symmetry of the dip if a dip is determined, and to indicate if the vessel is a ureter within the region proximate to the working end of the surgical instrument based on the ratio and the symmetry.

6. The system according to claim 1, further comprising the surgical instrument having the working end.

7. A method of determining if a ureter is within a region proximate to a working end of a surgical instrument, comprising:

administering a dye;

emitting light of two different wavelengths at the working end of the surgical instrument;

sensing light at the two different wavelengths at at least one light sensor array at the working end of the surgical instrument, the at least one light sensor array comprising an array of individual light sensors each configured to provide a signal having a direct current (DC) component;

determining a ratio of the light transmitted at the two different wavelengths;

determining a dip or decrease in the DC component of the signal between a first end and a second end of the at least one light sensor array in the DC component of the signal from the individual light sensors of the at least one light sensor array, determining a symmetry of the dip about an axis of symmetry if a dip is determined, and indicating if the ureter is within the region proximate to the working end of the surgical instrument based on the ratio and the symmetry.

8. The method according to claim 7, wherein determining the symmetry of the dip comprises:

determining, for each wavelength, a first distance from a first edge of the dip where the dip begins to a minimum of the dip where the DC component is at its lowest valve and a second distance from a second edge of the dip where the dip ends to the minimum; and subtracting the first distance from the second distance to define a difference.

9. The method according to claim 7, wherein:

sensing light of the two different wavelengths comprises sensing light at a first wavelength in the visible range and at a second wavelength in the near-infrared range.

10. The method according to claim 7, wherein administering the dye comprises continuously administering a dye intravenously throughout a surgery.

* * * * *